United States Patent
Ge et al.

(10) Patent No.: US 11,779,575 B2
(45) Date of Patent: Oct. 10, 2023

(54) USE OF WNT INHIBITOR WNT-C59 IN PREPARATION OF DRUG FOR TREATING SCN5A MUTATION-INDUCED DILATED CARDIOMYOPATHY

(71) Applicant: ZHONGSHAN HOSPITAL, FUDAN UNIVERSITY, Shanghai (CN)

(72) Inventors: Junbo Ge, Shanghai (CN); Aijun Sun, Shanghai (CN); Jingjing Hu, Shanghai (CN); Kun Yang, Shanghai (CN)

(73) Assignee: ZHONGSHAN HOSPITAL, FUDAN UNIVERSITY, Shanghai (CN)

(*) Notice: Subject to any disclaimer, the term of this patent is extended or adjusted under 35 U.S.C. 154(b) by 0 days.

(21) Appl. No.: 17/637,455

(22) PCT Filed: Aug. 6, 2021

(86) PCT No.: PCT/CN2021/111105
§ 371 (c)(1),
(2) Date: Feb. 23, 2022

(87) PCT Pub. No.: WO2022/116583
PCT Pub. Date: Jun. 9, 2022

(65) Prior Publication Data
US 2022/0370428 A1    Nov. 24, 2022

(30) Foreign Application Priority Data
Dec. 4, 2020 (CN) .......................... 202011403201.8

(51) Int. Cl.
*A61K 31/444* (2006.01)
*A61P 9/04* (2006.01)

(52) U.S. Cl.
CPC .............. *A61K 31/444* (2013.01); *A61P 9/04* (2018.01)

(58) Field of Classification Search
CPC .............................. A61K 31/444; A61P 9/04
See application file for complete search history.

(56) References Cited

U.S. PATENT DOCUMENTS 10,624,949 B1    4/2020    Negrete et al.

FOREIGN PATENT DOCUMENTS

CN    102369187 A    3/2012
CN    112472701 A    3/2021

OTHER PUBLICATIONS

Aizhu Lu, et al., Direct and Indirect Suppression of Scn5a Gene Expression Mediates Cardiac Na+ Channel Inhibition by Wnt Signalling, Canadian Journal of Cardiology, 2019.
Aijun Sun, et al. Altered Cardiac Sodium Channel Function Due to Voltage-Sensor Mutation in Dilated Cardiomyopathy Patients with SCN5A Mutations, Proceedings of the 15th National Academic Conference on Cardiovascular Diseases of the Chinese Medical Association, 2013.
Dan Lu, et al. Dkk3 prevents familial dilated cardiomyopathy development through Wnt pathway, Laboratory Investigation, 2016, pp. 239-248, 96.
Dai, Xiyan, et al., Research progress on the relationship between Wnt /β-catenin signaling pathway and arrhythmogenic right ventricular cardiomyopathy, Chinese Journal of Cardiac Pacing and Electrophysiology, 2012, pp. 476-477, vol. 26 No.6.
Aurelija Abraityte, et al. Wnt5a is associated with right ventricular dysfunction and adverse outcome in dilated cardiomyopathy, Scientific Reports, 2017, pp. 1-10, 7: 3490.
Liu Jingwen, et al., Aberrant expression profile of mRNA in dilated cardiomyopathy by RNA-sequence, Chin J Heart Fail & Cardiomyopathy, 2018, vol. 2 No. 3.
Wan Wei, et al., Current Status of Research in Dilated Cardiomyopathy Pathogenesis in Ion Channels, Adv Cardiovasc Dis, 2012, pp. 551-553, vol. 33 No.4.

*Primary Examiner* — Kevin E Weddington
(74) *Attorney, Agent, or Firm* — Bayramoglu Law Offices LLC

(57) ABSTRACT

The use of a Wnt inhibitor Wnt-C59 in the preparation of a drug for treating SCN5A mutation-induced dilated cardiomyopathy (DCM) is provided. With SCN5A genotype detection as a breakthrough point, a Wnt pathway-specific inhibitor Wnt-C59 is used to inhibit the abnormal activation of the Wntβ-Catenin pathway caused by SCN5A gene mutation, thereby improving the prognosis of cardiac function in a patient with SCN5A gene mutation-induced DCM. In experiments, aging and adriamycin-induced DCM models are constructed, and the therapeutic effect of Wnt-C59 on DCM is detected through indexes such as changes in cardiac function and activation of related signal molecules, which provides a theoretical basis for use of Wnt-C59 in the clinical treatment of DCM. A new treatment method for SCN5A mutation-induced DCM is provided to bring dawn to such patients and has promising application prospects.

8 Claims, 2 Drawing Sheets

USE OF WNT INHIBITOR WNT-C59 IN PREPARATION OF DRUG FOR TREATING SCN5A MUTATION-INDUCED DILATED CARDIOMYOPATHY

CROSS REFERENCE TO THE RELATED APPLICATIONS

This application is the national phase entry of International Application No. PCT/CN2021/111105, filed on Aug. 6, 2021, which is based upon and claims priority to Chinese Patent Application No. 202011403201.8, filed on Dec. 4, 2020, the entire contents of which are incorporated herein by reference.

TECHNICAL FIELD

The present disclosure relates to the technical field of biomedicine, and in particular to use of a Wnt inhibitor Wnt-C59 in the preparation of a drug for treating SCN5A mutation-induced dilated cardiomyopathy (DCM).

BACKGROUND ART

Primary DCM refers to the irreversible cardiac functional degradation caused by cardiac dilatation, with a prevalence of about 40/100,000 and a 5-year mortality of 50%. There is no specific therapeutic plan at present. About 20% to 30% of DCM cases are hereditary. It was originally discovered that pathogenic genes of DCM mostly encode cell structure proteins, such as cardiac actin gene and nuclear lamina protein (lamin A/C) gene, which cause myocardial damage and cardiac dilatation through damage to the stress transfer of cells. In 2004, McNair first proposed that mutations of the cardiac sodium channel gene (SCN5A) are related to DCM.

A functional unit of the cardiac sodium channel encoded by the SCN5A gene is composed of 4 homologous regions (DI to DIV), and each homologous region is composed of 6 transmembrane fragments S1 to S6. The fragment S4 is rich in positively charged residues and is a voltage sensor of the channel protein. Interestingly, both R225Q and A226V are located in the segment S4 of the region DI, that is, in addition to the 2 synonymous mutations, 80% (4/5) of the SCN5A mutations found are located in the voltage sensor of the channel. Previous studies have proved that the SCN5A mutations R814W and T220I related to DCM are also located in the voltage sensor. Struyk has reported that mutations in the voltage sensor of the skeletal muscle sodium channel can produce a gating pore effect, leading to abnormal hydrogen ion leakage, and the continuous hydrogen ion leakage can cause abnormal skeletal muscle function by interfering with the intracellular pH. In the previous research, according to the candidate gene sequencing analysis for the DCM family, a series of new SCN5A mutations A1180V, R225Q, A226V, I1448N, I94, and Y1434 were found, and it was confirmed that a series of SCN5A mutants are related to DCM. However, the corresponding pathogenesis and clinical applications are still unsuspected. Based on this, the following hypothesis is provided: mutations in the voltage sensor of the cardiac sodium channel gene bring unique abnormal currents to cause intracellular environmental disruption (such as changes in pH and $Ca^{2+}$ balance), thereby resulting in myocardial structural damage and dysfunction.

Previous studies have shown that the Wnt signaling pathway plays a key role in the regulation of cardiovascular development and myocardial hypertrophy. The Wnt signaling pathway is particularly active during cardiac development. The Wnt signaling pathway is static in a normal adult mammalian heart, but the Wnt signaling pathway will be activated during a cardiac pathological process. Studies have shown that the Wnt signaling is involved in processes such as cardiac ventricular remodeling, myocardial hypertrophy, and cardiac failure. Related studies have further shown that differentially expressed mRNAs are significantly enriched in the Wnt signaling pathway, and thus it can be inferred that the occurrence and development of DCM may be related to the activation of the Wnt signaling pathway and the intervention in this pathway may provide a new target for the treatment of DCM. On this basis, it is confirmed that, in a process of SCN5A-R225Q mutant-induced DCM, the Wnt signaling pathway is activated more significantly than the wild-type, indicating that the Wnt signaling pathway plays an important role in the process of SCN5A-R225Q mutant-induced DCM. The present disclosure proposes for the first time that the Wnt inhibitor Wnt-C59 can be used to treat SCN5A mutation-induced DCM. There is no report about use of the Wnt inhibitor Wnt-C59 of the present disclosure in the preparation of a drug for treating SCN5A mutation-induced DCM.

SUMMARY

In view of the shortcomings in the prior art, the present disclosure provides a new drug for treating SCN5A mutation-induced DCM.

To achieve the above objective, the present disclosure adopts the following technical solutions.

In a first aspect, the present disclosure provides the use of a Wnt inhibitor in the preparation of a drug for treating SCN5A mutation-induced DCM.

Further, the present disclosure provides the use of a Wnt inhibitor Wnt-C59 in the preparation of a drug for treating SCN5A mutation-induced DCM.

In a second aspect, the present disclosure provides the use of a Wnt inhibitor Wnt-C59 in the preparation of a drug for treating SCN5A-R225Q mutant-induced DCM.

Further, the present disclosure provides the use of a Wnt inhibitor Wnt-C59 in preparation of a drug for improving cardiac functions and prognosis of a patient with SCN5A-R225Q mutant-induced DCM.

Furthermore, the present disclosure provides the use of a Wnt inhibitor Wnt-C59 in the preparation of a drug for improving ventricular cavity enlargement, decreased myocardial contractility, and prognosis of a patient with SCN5A-R225Q mutant-induced DCM.

Preferably, a dosage form of the drug may be tablet, powder, suspension, capsule, pill, or syrup.

Those skilled in the art are well aware that the clinical manifestations and electrocardiograms of DCM diseases caused by different gene mutations show significant individual differences. In addition to SCN5A, genes causing DCM include MYH7, KCNQ1, ABCC9, CLIC2, and the like. In addition to common cardiac failure symptoms such as chest tightness, breathlessness, lower limb edema, decreased exercise tolerance, and dyspnoea, a patient may show electrocardiogram changes such as atrioventricular block (AVB), sinus bradycardia, sinus arrest, ventricular premature beat (VPB), ventricular tachycardia, complete bundle branch block (BBB), and symptoms such as dizziness, fatigue, syncope, and palpitation. Different DCM diseases caused by different gene mutations correspond to different clinical therapeutic plans. For example, since SCN5A is a gene encoding the $Na^+$ channel, corresponding DCM has the typical characteristic of arrhythmia, and common symptoms such as palpitation, dizziness, fatigue, and syncope; and since MYH7 is a gene encoding myosin, corresponding DCM has the typical manifestation of decreased myocardial contractility, and clinical manifestations such as chest tightness, breathlessness, dyspnoea, lower limb edema, and decreased exercise tolerance.

In addition, DCM diseases caused by different site mutations show significant differences in clinical symptoms, pathological features, and treatment methods. Specifically, in addition to common cardiac failure symptoms such as chest tightness, breathlessness, lower limb edema, decreased exercise tolerance, and dyspnoea, different site mutations may lead to different types of arrhythmia such as AVB, sinus bradycardia, sinus arrest, VPB, ventricular tachycardia, complete BBB, and symptoms such as dizziness, fatigue, syncope, and palpitation. Different DCM diseases caused by different site mutations correspond to different clinical therapeutic plans. Different pathological features will be presented due to different mutation sites, such as DCM pathological manifestations based on cardiac interstitial fibrosis, cardiomyocyte hypertrophy, and pathological manifestations based on inflammatory cell infiltration.

In addition to conventional cardiotonic, diuretic, vascular expansion, and ventricular remodeling improvement drug therapies, cardiac resynchronization therapy (CRT) is also widely used in clinical practice. If a patient has bradyarrhythmia such as AVB, sinus bradycardia, and sinus arrest, on the basis of standard treatment, a temporary pacemaker or a permanent dual-chamber/single-chamber pacemaker needs to be implanted according to the severity of symptoms of the patient. If a patient has tachyarrhythmia such as VPB and ventricular tachycardia, radiofrequency ablation (RFA) needs to be conducted or an implantable cardiac defibrillator (ICD) needs to be implanted.

Wnt-C59 is an inhibitor for Wnt protein activation, which can block the Wnt signaling pathway from the beginning. In tumor treatment experiments, Wnt-C59 can significantly inhibit the proliferation of 46 types of tumor cells. In this study, aging and adriamycin-induced DCM models are constructed, and the therapeutic effect of Wnt-C59 on DCM is detected through indexes such as changes in cardiac function and activation of related signal molecules, which provides a theoretical basis for use of Wnt-C59 in the clinical treatment of DCM.

The present disclosure has the following advantages:

On the basis of traditional standardized treatment, the present disclosure finds for the first time that SCN5A-R225Q mutant-induced DCM is related to the Wnt signaling pathway. With SCN5A genotype detection as a breakthrough point, a Wnt pathway-specific inhibitor Wnt-C59 is used to inhibit the abnormal activation of the Wntβ-Catenin pathway caused by SCN5A gene mutation to improve the prognosis of cardiac function in a patient with SCN5A gene mutation-induced DCM, which provides a theoretical basis for use of Wnt-C59 in the clinical treatment of DCM, a new target for the treatment of DCM, and a new treatment method for such patients. The inhibitor of the present disclosure can be well used in clinical practice, and has promising application prospects.

DETAILED DESCRIPTION OF THE EMBODIMENTS

Figure 1:
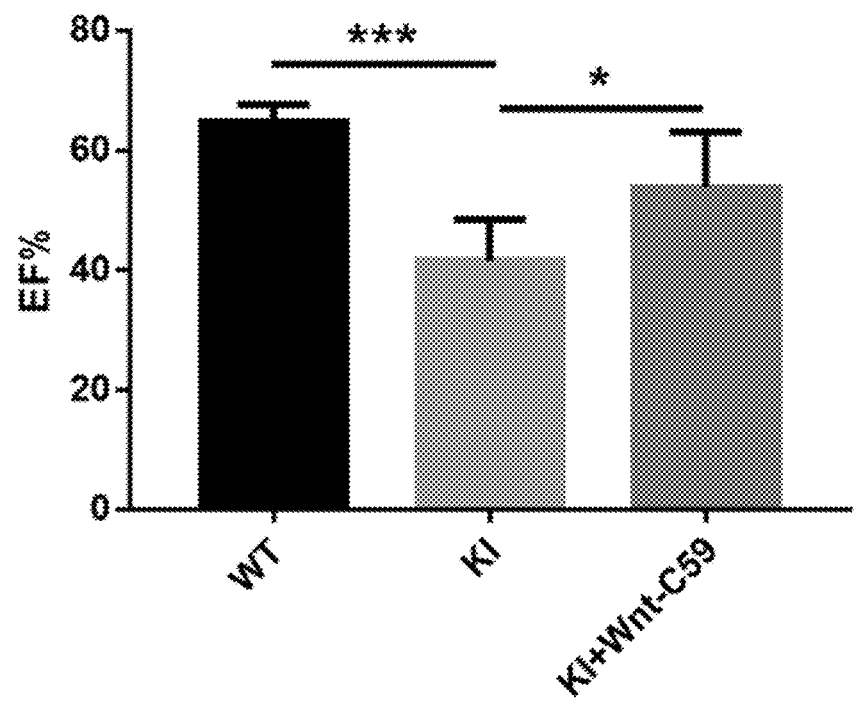
FIG. 1 shows left ventricular ejection fraction (LVEF) index results of mice in each group, where the results show that the cardiac function of mice in the KI+Wnt-C59 group is significantly improved after intragastric administration of Wnt-C59 (*: P<0.05; and ***: P<0.001).

The present disclosure will be further described below with reference to specific implementations. It should be understood that these examples are only intended to describe the present disclosure, rather than to limit the scope of the present disclosure. In addition, it should be understood that various changes and modifications may be made on the present disclosure by those skilled in the art after reading the content of the present disclosure, and these equivalent forms also fall within the scope defined by the appended claims of the present disclosure.

In this study, based on pre-clinical data of patients with DCM (that is, 90 sporadic DCM patients are subjected to SCN5A mutation screening), it is found that the R225Q mutation (c.674G>A) rate is the highest (a total of 3 cases), and the onset age of DCM is high (77, 55, and 80 years old).

EXAMPLE 1

Animal Experiment

1. Method
1.1 Preparation of Experimental Animals and Animal Models

SPF-grade male C57BL/6 mice (purchased from Shanghai Jiesijie Experimental Animal Co., Ltd.) and SCN5A heterozygous mutant mice (aging 8 to 10 weeks and weighing 20 g to 25 g) were selected and intraperitoneally injected with d-galactose (500 mg/kg. d, sigma G5388) continuously for 8 weeks to construct aging models. Then the mice were intraperitoneally injected with adriamycin (4 intraperitoneal injections, total 10 mg/kg, Sangon A603456) to construct DCM models. After the models were constructed, cardiomyocytes were isolated from mice in each of the KI group and the WT group. The experimental scheme was approved by the Animal Management and Ethics Committee of Fudan University.

The animal experiment showed that there was no statistical difference in the cardiac function between SCN5A heterozygous mutant mice and wild-type mice in natural aging models, pure galactose aging models, and pure adriamycin DCM models.

Early animal studies showed that, after being treated with galactose and adriamycin, SCN5A heterozygous mutant mice exhibited a DCM phenotype, namely, enlarged cardiac chamber, thinned left ventricular, and decreased ejection fraction, but the WT mice exhibited no cardiac function change. Cardiomyocytes were further isolated from mice in the KI group and the WT group and then subjected to Western blot assay, and results showed that the Wnt pathway was significantly activated in the KI group.

1.2 Grouping

After the ultrasonic test, there were 3 groups for study: WT group, KI group, and KI+Wnt-C59 group. Adriamycin was used for molding, and at the same time, the KI+Wnt-C59 group was intragastrically administered with Wnt-C59 (1 mg/kg.d, MCE HY-15659) every day, and the WT and KI groups were intragastrically administered with an equal volume of sterile normal saline as a control. Mice in each group received normal diet and water, and the administration was conducted continuously for 2 weeks. The body weight was measured and recorded for mice in each group every day.

1.3 Evaluation on Mouse Cardiac Function by Echocardiography

The echocardiogram was measured 2 weeks after the administration, with a probe frequency of 30 MHz. Specifically, the mice were anesthetized with isoflurane, and an M-mode image was recorded when a heart rate of the mice was maintained at 450 to 500 beats/min. B-Mode images were acquired along a parasternal long-axis section and an apical four-chamber section. Along a short axis of the parasternal left ventricle, a short-axis section of the left ventricle was shown by 2D ultrasound, and M-mode ultrasound was used to record the movement of the left ventricle at the papillary muscle level. Functional indexes included LVEF. The mice in the groups were compared in terms of the changes of cardiac morphology and function. All measurement values were average values of 5 consecutive cardiac cycles, which were conducted by 3 experienced technicians.

1.4 Detection of Wnt Pathway in Cardiomyocytes by Western Blot

Cardiomyocyte proteins were extracted separately from the KI group and WT group, and Western blot assay was conducted.

1.5 Material Collection

After 2 weeks of drug intervention, the mice were sacrificed and hearts thereof were collected for heart size comparison among the 3 groups.

Figure 2:
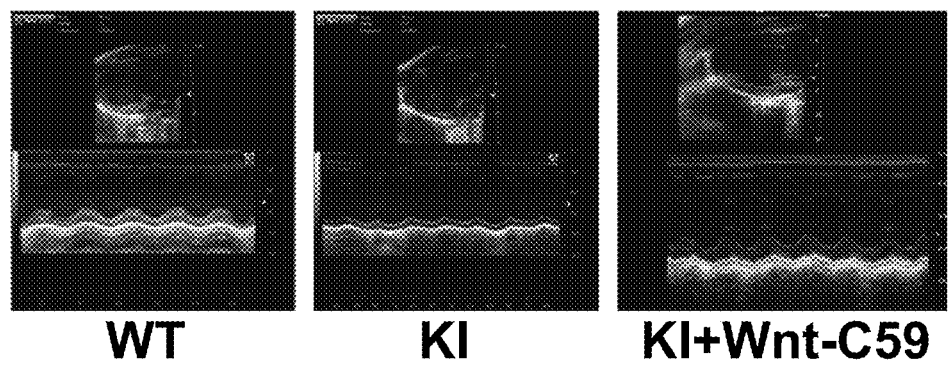
FIG. 2 shows M-mode images of mice in each group, where the results show that the cardiac function of mice in the KI+Wnt-C59 group is significantly improved after intragastric administration of Wnt-C59 (*: P<0.05; and ***: P<0.001).

2. Results 2.1 The results showed that the cardiac function index of mice in the KI group was significantly lower than that in the WT group, and the cardiac function of mice in the KI+Wnt-C59 group was improved. (as shown in FIG. 1 and FIG. 2)

Figure 3:
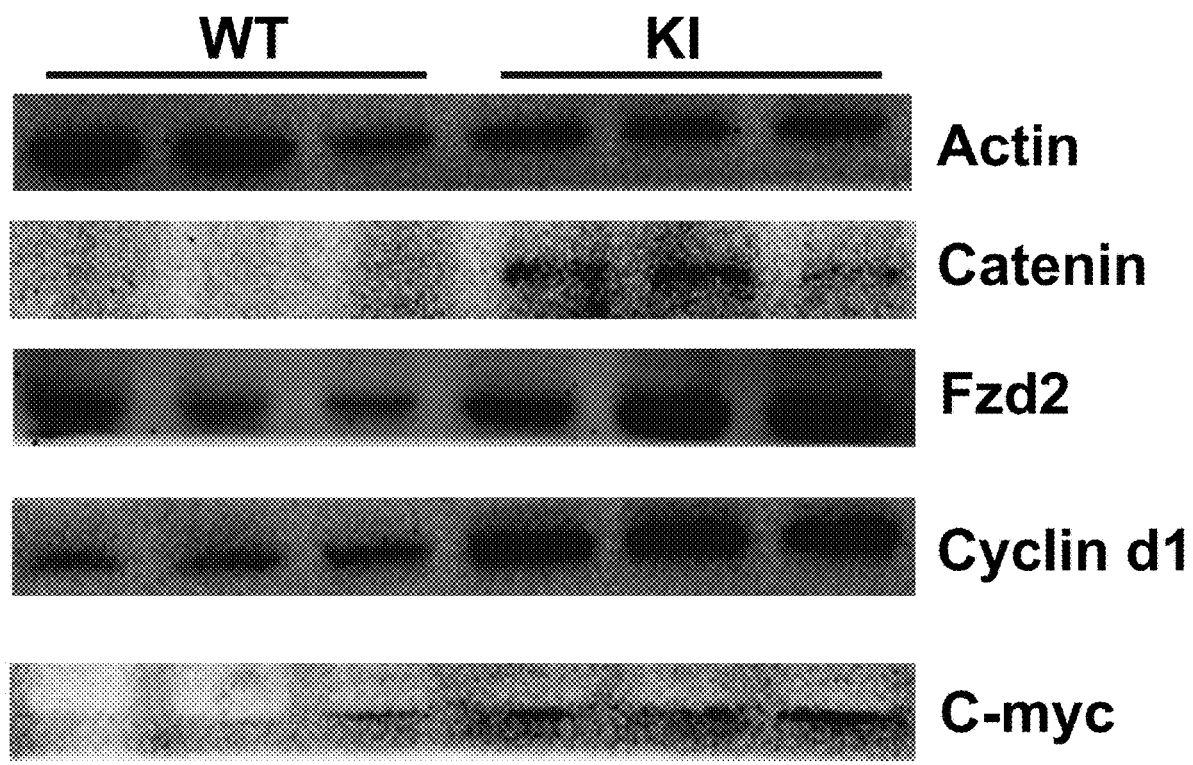
FIG. 3 shows Western blot detection results of mice in each group, where the results show that the Wnt pathway is significantly activated in the KI group compared with the Wnt pathway in the wide-type (WT) group.

2.2 The results showed that the Wnt pathway was significantly activated in the KI group. (as shown in FIG. 3)

Figure 4:
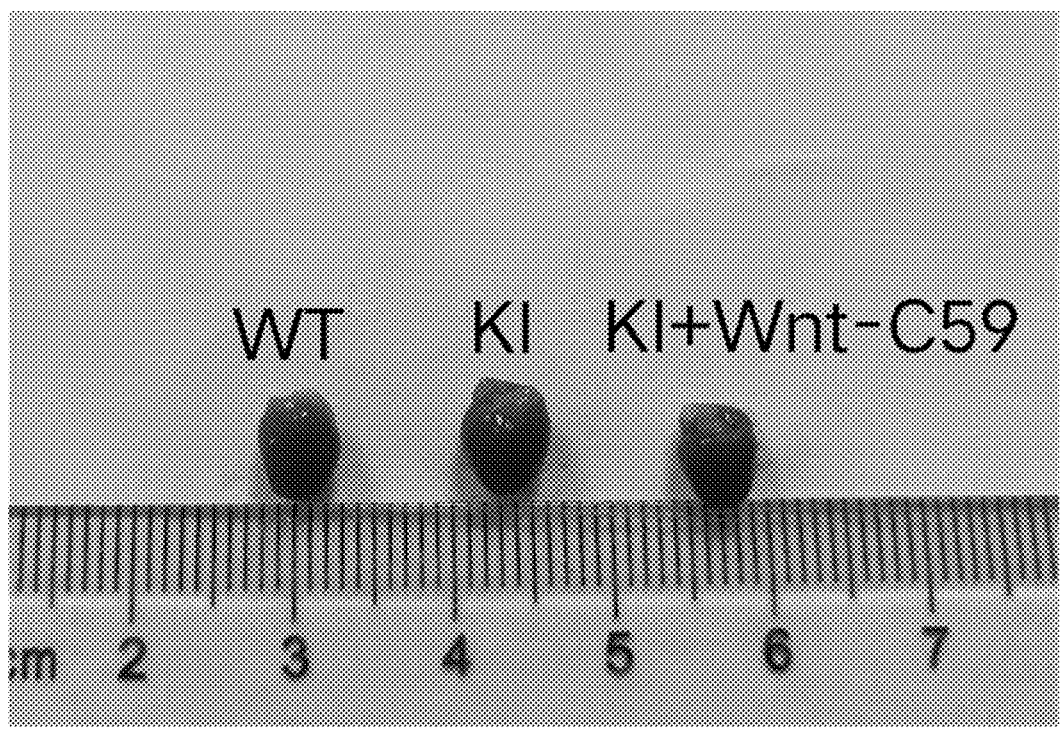
FIG. 4 shows heart sizes of mice in each group, where the results show that the heart of mice in the KI+Wnt-C59 group is significantly smaller than that in the KI group.

2.3 The results showed that the heart of mice in the KI+Wnt-C59 group was significantly smaller than that in the KI group. (as shown in FIG. 4)

3. Conclusion

The Wnt signaling is involved in processes such as cardiac ventricular remodeling, myocardial hypertrophy, and cardiac failure. The activation of Wnt signaling pathway is related to the occurrence and development of DCM. Based on research results herein, the Wnt signaling pathway inhibitor Wnt-C59 can significantly improve the cardiac function of aging and adriamycin-induced DCM mice, which provides a theoretical basis for use of Wnt-C59 in the clinical treatment of DCM and also provides a new target for the treatment of DCM.

Except for significantly inhibiting the proliferation of 46 types of tumor cells, Wnt-C59 as a new tumor proliferation inhibitor can improve the cardiac function of galactose-induced aging and adriamycin-induced DCM mice, which provides a theoretical basis for use of Wnt-C59 in the clinical treatment of DCM. Wnt-C59 is an important supplement to the traditional treatment of myocardial damage caused by DCM, such as cardiotonic, diuretic, and vascular expansion therapies, which can delay the progression of myocardial damage and improve the life quality of a patient.

The above descriptions are merely preferred implementations of the present disclosure. It should be noted that a person of ordinary skill in the art may further make several improvements and supplements without departing from the principle of the present disclosure, but such improvements and supplements should be deemed as falling within the protection scope of the present disclosure.

What is claimed is:

1. A method of treating a SCN5A mutation-induced dilated cardiomyopathy (DCM), comprising preparing a drug wherein the drug comprises a Wnt inhibitor Wnt-C59.

2. The method according to claim 1, wherein the SCN5A mutation-induced dilated cardiomyopathy (DCM) is a SCN5A-R225Q mutant-induced dilated cardiomyopathy (DCM).

3. The method according to claim 2, wherein the treatment further comprises improving cardiac functions and prognosis of a patient.

4. The method according to claim 2, wherein the treatment further comprises improving ventricular cavity enlargement, decreased myocardial contractility, and prognosis of a patient.

5. The method according to claim 1, wherein a dosage form of the drug is tablet, powder, suspension, capsule, pill, or syrup.

6. The method according to claim 2, wherein a dosage form of the drug is tablet, powder, suspension, capsule, pill, or syrup.

7. The method according to claim 3, wherein a dosage form of the drug is tablet, powder, suspension, capsule, pill, or syrup.

8. The method according to claim 4, wherein a dosage form of the drug is tablet, powder, suspension, capsule, pill, or syrup.

* * * * *